United States Patent [19]

Hsiung et al.

[11] Patent Number: 4,770,872
[45] Date of Patent: Sep. 13, 1988

[54] NEUTRALIZER FOR PERMANENTLY WAVING HAIR

[75] Inventors: Du Y. Hsiung, Park Forest; Norman L. Edelberg, Vernon Hills, both of Ill.

[73] Assignee: Helene Curtis Industries, Inc., Chicago, Ill.

[21] Appl. No.: 578,291

[22] Filed: Feb. 7, 1984

Related U.S. Application Data

[63] Continuation of Ser. No. 364,310, Apr. 1, 1982, abandoned, which is a continuation of Ser. No. 220,264, Dec. 29, 1981, abandoned.

[51] Int. Cl.$^4$ .......................... A61K 7/09; A61K 7/11
[52] U.S. Cl. .......................................... 424/71; 424/72
[58] Field of Search .................................... 424/71, 72

[56] References Cited

U.S. PATENT DOCUMENTS

| | | | |
|---|---|---|---|
| 3,842,848 | 10/1974 | Karjala | 424/71 |
| 3,865,930 | 2/1975 | Abegg et al. | 424/71 |
| 3,961,634 | 6/1976 | Busch | 424/71 |
| 4,349,537 | 9/1982 | Forbriger, Jr. | 424/71 |

*Primary Examiner*—Albert T. Meyers
*Assistant Examiner*—F. Krosnick
*Attorney, Agent, or Firm*—Dressler, Goldsmith

[57] ABSTRACT

A neutralizer for permanently waving hair containing water, an oxidant and about 0.05 to about 5 weight percent of a hydrolyzed animal protein derivative having quaternary nitrogen groups bonded to the protein amino groups, and a pH value of about 2 to 11. The hydrolyzed animal protein derivative has an isoionic point of at least 9.0 and a viscosity at 10 weight percent solids in water at 25° C. of about 5 to about 40 centipoises.

10 Claims, No Drawings

NEUTRALIZER FOR PERMANENTLY WAVING HAIR

CROSS-REFERENCE TO RELATED APPLICATIONS

This application is a continuation of application Ser. No. 364,310, filed Apr. 1, 1982, now abandoned; which is a continuation of application Ser. No. 220,264, filed on Dec. 29, 1981, now abandoned.

DESCRIPTION

1. Technical Field

This invention relates to permanent waves for hair, and particularly to a neutralizer for use in the permanent waving process.

2. Background Art

Permanent waving of hair is usually accomplished by first breaking disulfide bonds of the hair keratin to form keratin molecules within the hair fiber having at least some free —SH groups. After the disulfide bonds are broken, the keratin molecules are realigned within the hair so that the sulfur atoms which comprised the broken hair disulfide bonds are no longer adjacent one another. Thereafter, new disulfide bonds are formed within the hair so that the hair obtains a new configuration or wave. The new hair wave so imparted may be more curly or straighter (relaxed) than the original hair configuration.

In usual practice, the hair disulfide bonds are broken by a reagent having a free —SH group, such as thioglycolic acid, ammonium thioglycolate or glyceryl thioglycolate, or by a reagent, such as one containing a bisulfite ion, which generates a free —SH group upon reaction with the hair disulfide bond. The disulfide bond breaking reagent is usually dissolved in aqueous solution or in suspension, and the resulting composition is termed the waving lotion.

New disulfide bonds are formed within the hair by an aqueous composition termed the neutralizer. The neutralizer for a reagent having a free —SH group normally contains an oxidant, such as hydrogen peroxide or sodium bromate. For a reagent containing a bisulfite ion, the neutralizer contains an alkaline material to raise the pH value of the liquid in contact with the hair and thereby rebuild the hair disulfide bonds. After rinsing out the alkaline material, an oxidant, such as hydrogen peroxide, may be applied to the hair to help assure completeness of the disulfide bond rebuilding process. In addition, quaternary nitrogen compounds, such as that named Quaternium-31 in the *CTFA Cosmetic Ingredient Dictionary*, 2nd ed., published by the Cosmetic, Toiletry and Fragrance Association, Inc., 1977, and generally conforming to the formula $(CH_3)_2R_2N^+Cl^-$, wherein R represents a synthetic saturated alkyl group consisting primarily of 16 carbon atoms, are known to be useful as neutralizer components for imparting a conditioned feel to the waved hair after neutralization.

While many improvements have been made in hair waving compositions insofar as mildness to hair and skin, and product efficiencies are concerned, study of the hair fibers before and after waving processes are completed indicate that the cuticular layer on each hair fiber is usually damaged during waving. This damage is particularly noted after the waving process has been repeated several times. Cuticular damage is associated with an increased tendency toward fiber splitting and breakage, a roughened hair feel and a diminution in hair luster.

BRIEF SUMMARY OF THE INVENTION

According to this invention, a neutralizer for permanently waving (curling and straightening) hair is disclosed. This neutralizer has a pH value of about 2 to about 11 and contains water, an oxidant such as hydrogen peroxide, and about 0.05 to about 5 weight percent of a hydrolyzed animal protein derivative having quaternary nitrogen groups, preferably trimethylammonium groups, bonded to the amino groups of the hydrolyzed animal protein. The quaternary nitrogen group-containing hydrolyzed protein derivative has an isoionic point of at least about 9.0 and has a viscosity at about 10 weight percent solids in water at 25° C. of about 5 to about 40 centipoises.

Use of the neutralizer of this invention has several benefits and advantages over use of other, known permanent wave neutralizing compositions. Silient among these benefits and advantages is the fact that hair which is neutralized with the compositions of this invention exhibits better cuticular condition after waving than hair which is neutralized with other known neutralizing compositions. Thus, hair neutralized with the compositions of this invention shows less cuticular lifting and/or erosion than does hair neutralized with other known compositions.

DETAILED DESCRIPTION OF THE INVENTION

In accordance with the present invention, it has now been found that an unexpected improvement in hair cuticle condition may be achieved when about 0.05 to about 5 weight percent hydrolyzed animal protein derivative having quaternary nitrogen groups bonded to the hydrolyzed protein (or polypeptide) amino groups is incorporated into a neutralizing composition for the permanent waving of hair which also contains water, and an oxidant, and has a pH value of about 2 to about 11.

The hydrolyzed animal protein derivative contains quaternary nitrogen groups bonded to the chain terminal amino group residues and amino group termini of lysine residues. Thus, when in aqueous solution, the hydrolyzed animal protein derivative maintains a net positive charge under both acidic and basic conditions up to its isoionic point.

Quaternary nitrogen groups may be bonded to protein, hydrolyzed protein or polypeptide groups by one or more linking groups known in the art. It is preferred that the proteinaceous amino group of the final derivative be basic; i.e., as an amine rather than an amide, so that the resulting derivative has increased cationic character.

Examples of known linking groups are as follows: French Pat. No. 1,149,161 discloses acetyl linking groups which form amides with proteinaceous amino groups. *Chemical Abstracts* at 90: 209947S and 90: 174508V reports the use of 2-hydroxy-1,3-propylene groups between the proteinaceous material and quaternized amino group, leaving the preferred proteinaceous amino group basic. Most preferred linking groups are straight chain groups which contain about 12 to about 20 carbon atoms between the proteinaceous and quaternary nitrogen portions of the molecule. Examples of such linking groups include dodecylene, tetradecylene, hexadecylene and octadecylene. The octadecylene (stearene) group is particularly preferred for linking the quaternary nitrogen groups to the proteinaceous, basic amino groups.

Useful quaternary nitrogen groups include lower alkyl ammonium groups, such as trimethylammonium, triethylammonium and dimethylethylammonium, pyridinium groups, aralkylammonium groups, such as dimethylbenzylammonium wherein the alkyl groups are lower alkyl residues, and the like. As used herein, lower alkyl includes saturated straight or branched claims having up to four carbon atoms, and includes substituted radicals such as 2-hydroxyethyl. Trimethylammonium groups bonded to the hydrolyzed protein or polypeptide amino groups are preferred.

A useful way of characterizing the amount of quaternary nitrogen groups bonded to the hydrolyzed animal protein is by the isoionic point of the product. The isoionic point suitable for the quaternary nitrogen containing hydrolyzed animal proteins useful herein is at least about 9.0. More preferably, the isoionic point is about 9.5 to about 10.5.

Along with isoionic point, viscosity measurements are found useful for characterizing the hydrolyzed animal protein derivatives since viscosity is usually related to molecular weight for a series of related polymers such as proteins and their derivatives. Hydrolyzed animal proteins having quaternized nitrogen groups bonded to the amino residues thereof which, at 25° C. and at about 10 weight percent solids in water, have a viscosity between about 5 and about 40 centipoises (cps) are found suitable for use herein. More preferably, the viscosity under the above test conditions is from about 5 to about 15 cps. These viscosities are Brookfield viscosities measured on a model RVT Brookfield Viscometer using Spindle #1 at 50 revolutions per minute.

While several hydrolyzed animal protein derivatives may be useful herein, one material has been found particularly useful. This material has trimethylammonium groups bonded to the chain terminal amino groups and the lysine residue-terminal amino groups by stearenyl or octadecenyl linking groups [-(CH$_2$)$_{18}$], and is sold under the designation CROTEIN Q by Croda, Inc. of New York, N.Y. Another, similar commercially available material is sold under the designation QUAT-PRO S by Maybrook, Inc. of Union, N.J. The name adopted by the Cosmetics Toiletries and Fragrances Association for both of these products is Steartrimonium Hydrolyzed Animal Protein.

The specifications published for the product manufactured by Croda, Inc. indicate that as sold, it is an off-white, free-flowing powder, having a bland, not unpleasant odor. It has a maximum of about 7 percent moisture, leaves a maximum of about 5 percent ash on ignition, has a minimum nitrogen content of about 15.0 weight percent and a 1 percent solution in water gives a pH value of about 5.5 to about 7. The average molecular weight of this material is said to be about 12,500. The isoionic point of this commercial material is minimally about 9.5 to about 10.5. The manufacturer lists the viscosity of a 10 percent solids solution in water at 25° C. as being 23 to 33 mps. Determination of Brookfield viscosity as described hereinbefore, indicates a viscosity in the preferred range of about 5 to about 15 centipoises.

The above specification published by Croda, Inc. for CROTEIN Q states that that product is a hydrolyzed collagen in which quaternization of over 90 percent of the available amino groups has been achieved. This product is said to have the following schematic structure:

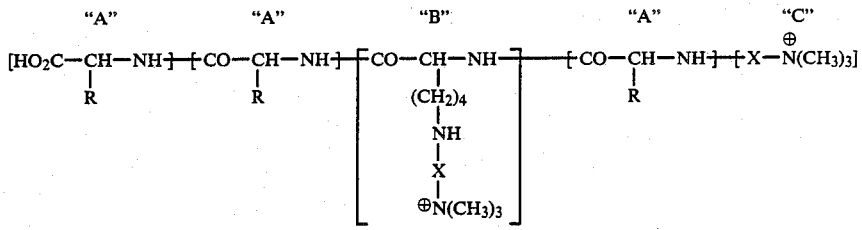

wherein
"A" represents chain amino acid residues,
"B" represents a quaternized lysine amino acid residue,
"C" represents a quaternized chain terminal amino acid residue,
"R" represents the various amino acid side chain groups, and
"X" represents the linking groups.

The hydrolyzed animal protein containing quaternary nitrogen groups bonded to the amino groups thereof may be used in the neutralizer compositions of this invention at about 0.05 to about 5 weight percent of the composition. Preferably, this protein derivative is utilized at about 0.1 to about 1 weight percent.

The use of hydrolyzed animal protein derivatives, such as the preferred CROTEIN Q, in waving lotions is known in the art, and Croda, Inc. recommends the use of CROTEIN Q in alkaline waving preparations because its quaternary charge allows substantivity to hair at high pH values. It has been found however, that use of a quaternary nitrogen-containing containing hydrolyzed animal protein, such as CROTEIN Q, in the neutralizer rather than in the waving lotion provides an unexpected benefit as to the condition of the hair cuticle.

For example, scanning electron microscope (SEM) studies indicate that when CROTEIN Q is utilized in a neutralizer, there is less cuticular lifting after one waving cycle of disulfide bond breakage and rebuilding than when this ingredient is used in the waving lotion at the same concentration, with the other ingredients and pH values of the compared waving lotion and neutralizer being held constant. After three waving cycles, this difference in use between the waving lotion and neutralizer is more pronounced. These results are described in more detail in Example 2, hereinafter.

The mechanism by which a hydrolyzed animal protein derivative such as CROTEIN Q works to better the condition of the cuticle is unknown. It is also unknown as to why there should be a difference between its use in the waving lotion and its use in the neutralizer. While not wishing to be bound by any hypothesis, it is believed that the substantivity to hair caused by the quaternized nitrogen groups, such as the trimethylammonium group, may play a role in affecting the cuticular condition. However, it is not known why a substantivity effect should be different in the observed direction between use in a waving lotion and a neutralizer.

Along with water and the hydrolyzed animal protein derivative, the neutralizers of this invention also contain an oxidant, as stated above. Materials such as hydrogen peroxide, which is preferred, water-soluble bromate and perborate salts, such as sodium bromate and sodium perborate, are well-known in the art as oxidants, and as being useful in neutralizing hair during the permanent waving process.

The amount of oxidant utilized in the neutralizers of this invention may vary based upon the amount of disulfide bond cleaving agent used, the speed with which neutralization is to be carried out and the oxidizing efficiency of the oxidant under the specific neutralization conditions selected, as in well-known in the waving art. When the preferred oxidant, hydrogen peroxide, is used as oxidant, it is suitably present at about 0.5 to about 3 weight percent, and preferably at about 1 to about 2.5 percent by weight.

It was surprising that a hydrolyzed animal protein derivative would be compatible with an oxidant since oxidants, such as hydrogen peroxide, are known to react with animal proteins to decolorize their solutions. Nevertheless, it has been found that when hydrogen peroxide is utilized with the preferred hydrolyzed animal protein derivative in the more preferred oxidant concentration range, only a slight amount of hydrogen peroxide is lost on aging, about 0.1 percent by weight. This loss occurred during the initial aging period and thereafter no increased loss of hydrogen peroxide was found over that normally expected.

The pH values of the neutralizing compositions of this composition are suitably about 2 to about 11. Again, the choice of the pH value is known in the hair waving art and may be selected to fit the particular waving system, as is also known. For example, sodium perborate oxidants are frequently utilized at a pH value of about 9.0 to about 10.5 in alkaline (about pH 9.4) ammonium thioglycolate waving systems. When so used, the sodium perborate is usually packaged separately as a solid and is dissolved in the remaining neutralizer composition prior to use. Hydrogen peroxide is usually used at a neutralizer pH value of about 3.5 to about 5.

In addition to the above-described components, the neutralizer of the present invention may also contain additional ingredients. These ingredients include, but are not limited to colorants, fragrances, buffers such as water-soluble citrate salts or phosphate salts, and the like. Quaternary nitrogen-containing molecules, such as the before described Quaternium-31, which add to the hair conditioning properties conferred by the hydrolyzed animal protein derivative may also be present.

The neutralizer compositions of this invention may generally be prepared by admixture with water of the desired amount of hydrolyzed animal protein derivative having quaternary nitrogen groups bonded thereto and agitation of the admixture until a substantially homogeneous solution is prepared. The oxidant, such as hydrogen peroxide, is admixed and agitated thereafter until the composition is substnatially homogeneous. The pH value of the composition is thereafter adjusted to between about 2 and about 11 as is desired for the particular product.

The compositions of this invention are used after the disulfide breaking or cleaving reagent has been rinsed from the hair. Typically, about four fluid ounces are utilized per head of hair, and this amount is in large part determined by the oxidant selected, its degree of water-solubility and its amount. The neutralizer is typically left on the head for about 5 minutes prior to rinsing it out.

The compositions of this invention are illustrated by, but not limited to, the examples which follow.

Best Mode For Carrying Out The Invention

EXAMPLE 1

Permanent Waving Neutralizer

A permanent waving neutralizer according to this invention was prepared by dissolving Steartrimonium Hydrolyzed Animal Protein (0.5 weight percent of the final composition) in water at 26° C. followed by cooling to ambient temperature, addition and admixture of sufficient hydrogen peroxide (35 percent by weight) to provide a final concentration of about 2.2 percent by weight. Thereafter, the pH value of the composition was adjusted to 4.5, and the remainder of the required water was added and mixed to provide a substantially homogeneous composition.

EXAMPLE 2

Comparison of Steartrimonium Hydrolyzed Animal Protein in Waving Lotion vs. Neutralizer A waving lotion was prepared having the following ingredients:

| Ingredient | Percent by Weight |
| --- | --- |
| Water, deionized | 84.35 |
| Ammonium thioglycolate (60% as thioglycolic acid) | 9.30 |
| Ammonium hydroxide (28% NH$_3$) | 0.25 |
| Ammonium bicarbonate | 5.40 |
| Potassium Coco-hydrolyzed Animal Protein (Note 1) | 0.50 |
| Fragrance | 0.20 |
| | 100.00 | pH value of several preparations = 7.5–7.7
Note 1. The potassium salt of the reaction product of coco-fatty acid and hydrolyzed animal protein was used. This material is sold under the designation MAYPON 4C by Stepan Chemical Company.

Five tresses of virgin (unchemically treated) brown hair (DeMeo Brothers, New York, N.Y.) were prepared, waved as follows, rinsed, dried, shampooed and dried again. The first tress was waved once using the above waving lotion and the neutralizer of Example 1. A second tress was waved three times with these compositions. The third tress was waved once using the above waving lotion containing 0.5 weight percent Steartrimonium Hydrolyzed Animal Protein (CROTEIN Q) in place of an equal weight of water, and the neutralizer of Example 1 wherein water replaced the CROTEIN Q. The fourth tress was waved three times with the latter-mentioned compositions. All of the four tresses were waved using substantially identical waving conditions (below). The fifth tress was saved as a control and remained untreated.

In carrying out the waving process, the tress was first shampooed with a commercially available product, rinsed thoroughly and then blotted with a towel. The thus dampened hair was then saturated with the waving lotion, using about 2–3 milliliters of waving lotion per tress, and the waving lotion combed through the hair once. The hair was then wound on waving rods (rollers). The wound hair was resaturated with waving lotion using a 15 minute waiting period between saturations to simulate the time usually taken between saturation steps when hair is waved on a person. The resaturated, wound tress was thereafter placed beneath a plastic turban and under a heated hair dryer, set on the high setting, for a 12 minute processing time.

After processing, the waving lotion was thoroughly rinsed from the hair using a warm water rinse. The wound, rinsed hair was towel blotted, then saturated with the neutralizer composition, again using about 2-3 milliliters per tress. Five minutes after neutralization, the waving rods were removed and the neutralizer was worked gently through the hair for about 1 minute by finger massage. The neutralized hair was then rinsed thoroughly with lukewarm water, dried, shampooed and air dried.

Ten fibers from the center portion of each tress were mounted so that the middle fiber portion was exposed to the SEM. After scanning each fiber in each group, a representative area was chosen from one fiber and a photo was taken at a magnification of 1000X.

Inspection of the photos showed that when the Steartrimonium Hydrolyzed Animal Protein was in the neutralizer, the hair cuticle was left in better condition than when it was in the waving lotion. The differences were best manifest on the three times waved hair. For those samples, while substantial cuticle lifting was noted for the neutralizer with protein derivative, there was no cuticlar breakage evident as was the case when the protein derivative was in the waving lotion. A similar, though less pronounced, difference was noted for the singly waved hair.

EXAMPLE 3

Half-Head Comparisons Against a Conventional Neutralizer Composition With Differing Waving Lotions In a first demonstration, 5 models' hair were waved using the waving lotion whose formula is shown in Example 2, with the addition of 0.5 weight percent CROTEIN Q replacing an equal amount of water. After a double saturation of the model' hair with waving lotion, as discussed for the tresses of Example 2, the hair was covered with a plastic turban within a heated, salon-type hair dryer. Processing times under the dryer were 12 minutes for models with normal hair and 6 minutes for models with tinted hair. The waving lotion was thereafter thoroughly rinsed from the hair using warm water.

The hair on one side of a hypothetical line drawn from the nose to the nape of the model's neck (half-head) was neutralized using a neutralizer containing 91.25 weight percent water, 1.5 weight percent of 75 percent active Quaternium-31, 6.23 weight percent of 35 percent hydrogen peroxide and about 0.01 weight percent each of phosphoric acid and a defoaming agent; the final pH value being 3.5. The other half-head was neutralized with a composition of this invention in which two-thirds (1 weight percent of the total composition) of the 75 percent active Quaternium-31 was replaced by an equal amount of CROTEIN Q.

Ten fibers were cut from each side of the models' heads and were examined under the SEM in a manner similar to that described in Example 2. The photos showed that all five of the sides treated with the neutralizer of this invention showed less cuticle lifting than did hair neutralized with the conventional conditioning neutralizer.

A second half-head demonstration was carried out on the hair of 2 models using a commercially available waving lotion which contained glyceryl thioglycolate at pH 6.9 as the disulfide bond cleaving agent. Package directions were followed through the rinse out of the waving lotion. Thereafter, half-head determinations as herein above described were carried out.

The SEM photographs again showed better cuticle condition for hair neutralized with the composition of this invention.

The invention is defined by the claims which follow.

I claim:

1. In a neutralizer for permanently waving hair comprising water and an oxidant, the improvement wherein said neutralizer contains about 0.05 to about 5 weight percent hydrolyzed animal protein derivative having quaternary lower alkyl ammonium groups bonded to the chain terminal amino residues and amino group termini of lysine residues of the protein, said hydrolyzed animal protein derivative having an isoionic point of at least about 9.0 and a viscosity at about 10 weight percent solids in water at 25° C. of about 5 to about 40 centipoises, said neutralizer having a pH value of about 2 to about 11, and providing reduced cuticle lifting and/or erosion to the hair.

2. The neutralizer according to claim 1 wherein said quaternary nitrogen group is trimethylammonium.

3. The neutralizer according to claim 1 wherein said hydrolyzed animal protein derivative is present at about 0.1 to about 1 weight percent.

4. The neutralizer according to claim 1 wherein said neutralizer has a pH value of about 3.5 to about 5.

5. In a neutralizer for permanently waving hair comprising water and an oxidant, the improvement wherein said neutralizer contains about 0.1 to about 1 weight percent hydrolyzed animal protein derivative having trimethylammonium groups bonded to chain terminal amino residues and amino group termini of lysine residues of the protein, said hydrolyzed animal protein derivative having an isoionic point of at least about 9.5 and a viscosity at about 10 weight percent solids in water at 25° C. of about 5 to about 40 centipoises, said neutralizer having a pH value of about 3.5 to about 5, and providing reduced cuticle lifting and/or erosion to the hair.

6. The neutralizer according to claim 5 wherein said oxidant is hydrogen peroxide.

7. The neutralizer according to claim 5 wherein said isoionic point of said hydrolyzed protein derivative is about 9.5 to about 10.5.

8. The netralizer according to claim 5 wherein said viscosity of said hydrolyzed protein derivative is about 5 to about 15 centipoises.

9. A neutralizer for permanently waving hair comprising water, about 0.5 to about 3 weight percent hydrogen peroxide and about 0.1 to about 1 weight percent hydrolyzed animal protein derivative having trimethylammonium groups bonded to chain terminal amino residues and amino group termini of lysine residues thereof, said hydrolyzed animal protein derivative having an isoionic point of about 9.5 to about 10.5 and a viscosity at about 10 weight percent solids in water at 25° C. of about 5 to about 15 centipoises, said neutralizer having a pH value of about 3.5 to about 5, and providing reduced cuticle lifting and/or erosion to the hair.

10. A neutralizer for permanently waving hair comprising water, about 0.5 to about 3 weight percent hydrogen peroxide and about 0.1 to about 1 weight percent hydrolyzed collagen derivative having trimethylammonium groups bonded to chain terminal amino residues and amino group termini of lysine residues thereof by straight chain linking groups containing about 12 to about 20 carbon atoms, said hydrolyzed collagen derivative having an isoionic point of about 9.5 to about 10.5 and a viscosity at about 10 weight percent solids in water at 25° C. of about 5 to about 15 centipoises, said neutralizer having a pH value of about 3.5 to about 5, and providing reduced cuticle lifting and/or erosion to the hair.

* * * * *